US009395289B2

(12) United States Patent
Manuel

(10) Patent No.: US 9,395,289 B2

(45) Date of Patent: Jul. 19, 2016

(54) TOOL FOR MEASURING UNDERCARRIAGE WEAR

(71) Applicant: Donald Manuel, Fairhope, AL (US)

(72) Inventor: Donald Manuel, Fairhope, AL (US)

( * ) Notice: Subject to any disclaimer, the term of this patent is extended or adjusted under 35 U.S.C. 154(b) by 0 days.

(21) Appl. No.: 14/318,511

(22) Filed: Jun. 27, 2014

(65) Prior Publication Data

US 2015/0007633 A1 Jan. 8, 2015

Related U.S. Application Data

(60) Provisional application No. 61/843,290, filed on Jul. 5, 2013.

(51) Int. Cl.

| | |
|---|---|
| ***B61K 9/12*** | (2006.01) |
| ***G01N 3/56*** | (2006.01) |
| ***B64C 25/00*** | (2006.01) |
| ***B64F 5/00*** | (2006.01) |
| ***G01M 99/00*** | (2011.01) |
| ***G01B 3/22*** | (2006.01) |
| ***G01B 5/00*** | (2006.01) |
| *B64D 45/00* | (2006.01) |

(52) U.S. Cl.

CPC .. *G01N 3/56* (2013.01); *B61K 9/12* (2013.01); *B64C 25/001* (2013.01); *B64F 5/0045* (2013.01); *G01B 3/22* (2013.01); *G01B 5/0025* (2013.01); *G01M 99/007* (2013.01); *B64D 2045/008* (2013.01)

(58) Field of Classification Search

None

See application file for complete search history.

(56) References Cited

U.S. PATENT DOCUMENTS

| | | | | |
|---|---|---|---|---|
| 3,188,464 A * | 6/1965 | Gieskieng | B61K 9/12 | 246/169 R |
| 4,176,463 A * | 12/1979 | Ringle | G01B 5/255 | 33/203.18 |
| 4,268,968 A * | 5/1981 | Przybylinski et al. | 33/548 | |
| 4,392,305 A * | 7/1983 | Nix et al. | 33/834 | |
| 4,802,285 A * | 2/1989 | Ligacz | B23B 5/28 | 33/203.11 |
| 8,439,315 B2 * | 5/2013 | Kilian | B61K 9/06 | 246/167 R |
| 2007/0044330 A1 * | 3/2007 | Moffett | B61K 9/12 | 33/203.18 |

* cited by examiner

*Primary Examiner* — Charlie Y Peng

(74) *Attorney, Agent, or Firm* — Garrett James O'Sullivan; Timothy Marc Shropshire; MU Patents

(57) ABSTRACT

An undercarriage wear measurement tool includes a housing with an elongated passage. A sleeve is attached to the proximal end of the housing for centering over a component, such as, a bolt head therewith and includes a fastener magnet for attaching to a metal component. The undercarriage wear measurement tool includes an elongated measurement pin slidably disposed within the elongated passage.

2 Claims, 3 Drawing Sheets

64 20 24 26 60 70 52 22 28 10 66 B 68 C

TOOL FOR MEASURING UNDERCARRIAGE WEAR

CROSS-REFERENCE TO RELATED APPLICATIONS

The present application claims the benefit of U.S. Provisional Application No. 61/843,290, filed Jul. 5, 2013, which application is incorporated herein by reference.

BACKGROUND OF THE INVENTION

Excavators, dozers, and backhoes are a few examples of heavy equipment commonly used at, for example, mining, forestry or construction sites. Most types of heavy equipment are mobile, and the drive system may include wheels or a track-type undercarriage. A continuous track undercarriage is typically used to move the heavy equipment and large amounts of material over dirt or natural type terrain. Track undercarriages include a track assembly underneath the equipment on each side in place of axels and wheels on wheeled equipment. Depending on the environment, the undercarriage track can be exposed to hard rock that can infiltrate into the undercarriage causing damage to the components. To reduce damage to the lower rollers caused by rooks, the undercarriage may be equipped with roller guards sometimes referred to as rook guards. Roller guards are heavy metal shields that cover the rollers of an undercarriage and reduce the ability for rocks and/or other foreign debris from entering the roller areas causing premature wear and damage to the undercarriage. To maintain the safety and performance of the heavy equipment manufacturers suggest that the undercarriage be inspected as part of the routine maintenance. During the routine maintenance of a machine, it is necessary to check the condition of individual undercarriage components by measuring the amount of wear. To measure undercarriage rollers with roller guards installed, the bucket of the machine is pushed into the ground to lift the equipment and expose the rollers. Once the machine is lifted and the rollers are exposed, a hand held caliper is used to manually measure the diameter of the roller. As a result of the inherent dangers of measuring undercarriage rollers with roller guards, roller wear is rarely measured.

BRIEF SUMMARY OF THE INVENTION

In accordance with the purposes of the present invention, as embodied and broadly described herein, the present invention includes an undercarriage wear measurement tool having a housing with an elongated passage. A sleeve is attached to the proximal end of the housing for centering over a component bolt head therewith and includes a fastener magnet for attaching to a metal component. The undercarriage wear measurement tool includes an elongated measurement pin slidably disposed within the elongated passage.

BRIEF DESCRIPTION OF THE DRAWINGS

The description herein makes reference to the accompanying drawings wherein like reference numerals refer to like parts throughout the views, and wherein.

DETAILED DESCRIPTION OF THE INVENTION

Figure 1:
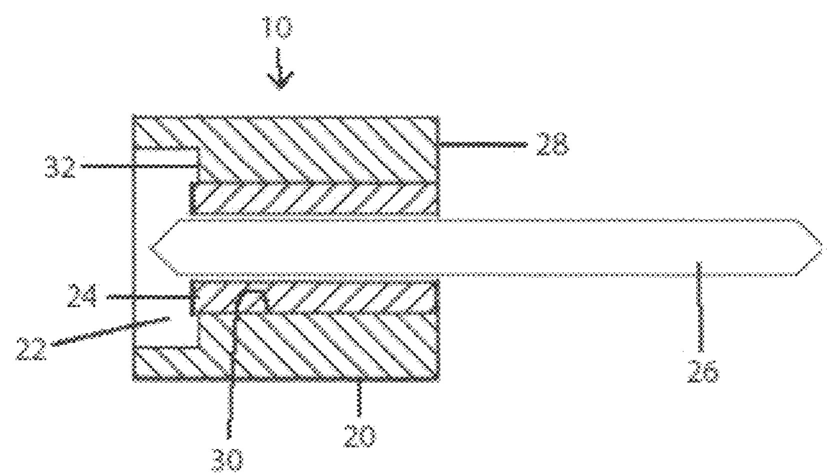
FIG. 1 is a schematic view of an exemplary undercarriage wear measurement tool including a sleeve.
Figure 1:
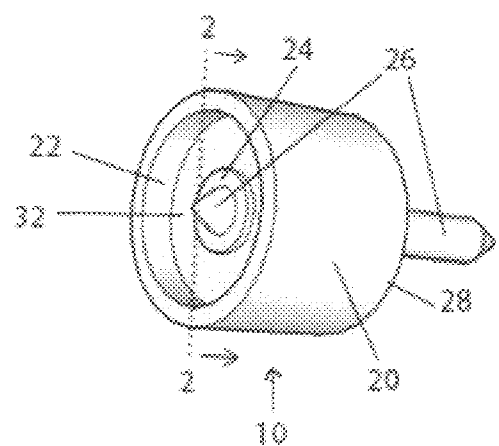
Figure 2:
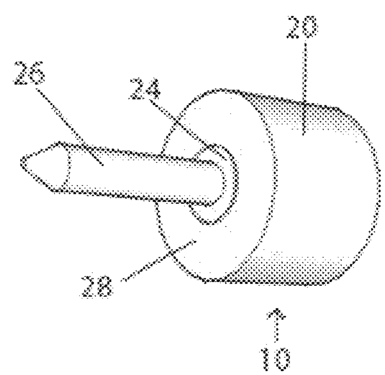
FIG. 2 is a schematic view of an exemplary undercarriage wear measurement tool having a flat surface.
Figure 3:
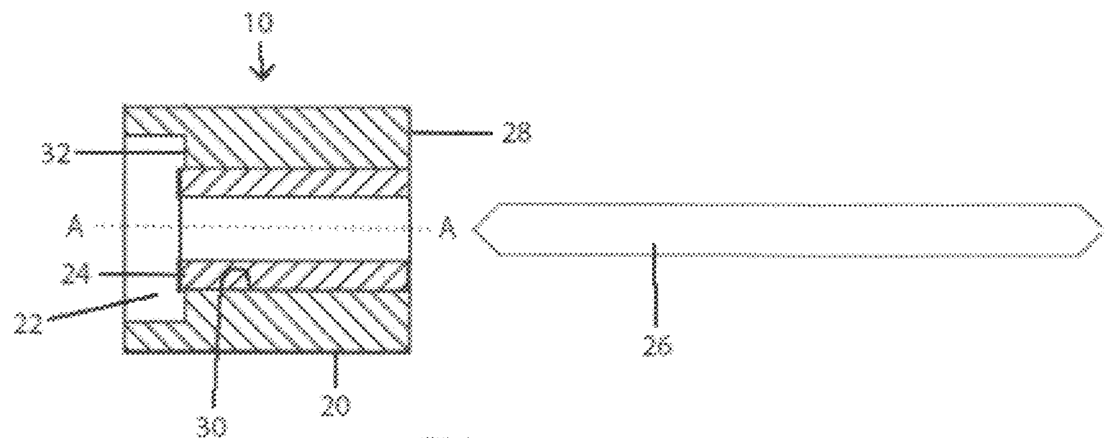
FIG. 3 is a side cross-sectional view of the undercarriage wear measurement tool taken along section 2-2 of FIG. 1, illustrating a measurement pin removed.
Figure 4:
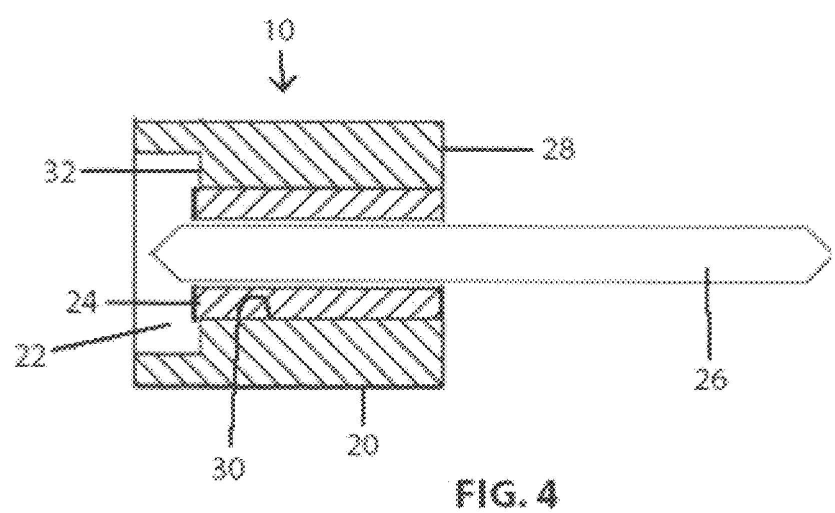
FIG. 4 is a side cross-sectional view of the undercarriage wear measurement tool taken along section 2-2 of FIG. 1, illustrating a measurement pin installed.

Referring now to the discussion that follows and also to the drawings, illustrative approaches to the disclosed invention are shown in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

Figure 5:
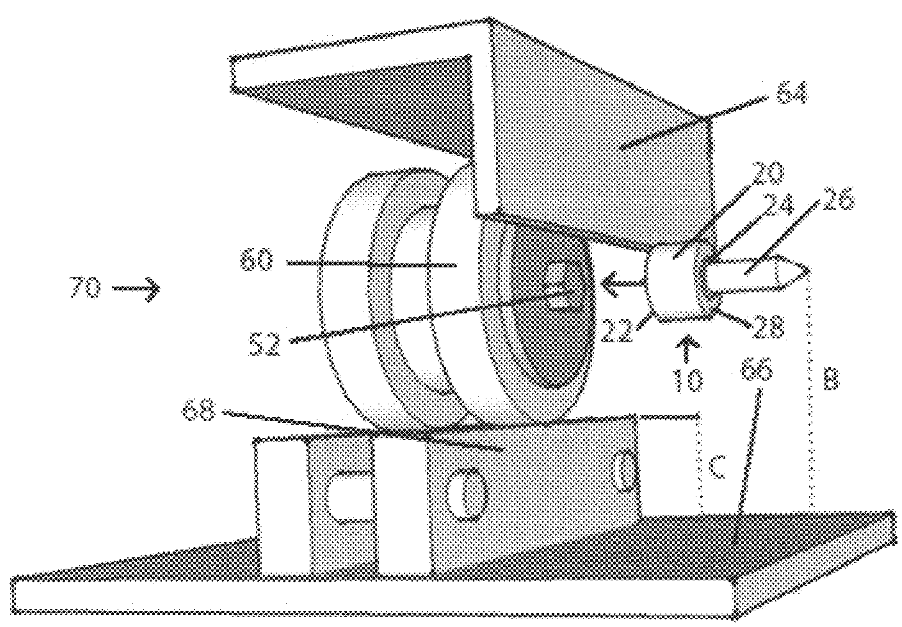
FIG. 5 is a schematic view of a portion of a track type undercarriage, including a schematic view of an exemplary undercarriage wear measurement tool.

Referring to FIGS. 1-4, an exemplary undercarriage wear measurement tool 10 may include a housing 20 having an elongated internal passage 30 extending lengthwise along a longitudinal axis A-A of housing 20. Internal passage 30 may extend entirely through housing 20 from a proximal end 32 to an opposite flat surface distal end 28. Attached to proximal end 32 of housing 20 is a sleeve 22 configured for receiving a component, for example, a conventional bolt head 52, as illustrated in FIG. 5. The sleeve 22 may be fixedly attached to housing 20, such as by welding, brazing, soldering and gluing, to name a few, or integrally formed with housing 20. For purposes of discussion, sleeve 22 is illustrated as being integrally formed with housing 20. The exemplarily configuration for housing 20 are shown in FIGS. 1-5 as cylinder shaped and may alternatively employ other non-circular shapes, for example, square, rectangular, triangular and polygonal, to name a few.

With continued reference to FIGS. 1-4, undercarriage wear measurement tool 10 may include one or more fastener magnets 24 disposed within internal passage 30 of housing 20 for reasonably securing the undercarriage wear measurement tool to the component being measured. Alternatively, fastener magnet 14 may not extend the complete length of internal passage 30 or may be outside the internal passage 30. For purposes of discussion, fastener magnet 24 is illustrated as within the complete length of internal passage 30.

Undercarriage wear measurement tool 18 may include an elongated measurement pin 28 disposed within internal passage 30 of housing 20. A longitudinal axis of measurement pin 26 may substantially coaxially align with longitudinal axis A-A.

Exemplary undercarriage wear measurement tool 10 may be used in a variety of applications, including but not limited to, measuring wear of lower roller 60 of a heavy equipment track type undercarriage 70, as illustrated in FIG. 5. A portion of a track type undercarriage 70 which is schematically illustrated in FIG. 5 may include components such as a track shoe 66, a track link 68, and a lower roller 10. An exemplary undercarriage lower roller 60 may be attached to a heavy equipment undercarriage 70 by a lower roller bolt 52. The lower roller 60 of an undercarriage 70 may be enclosed within a roller guard 64 for protection.

The need to calculate lower roller 60 wear is essential to determine the life remaining of lower roller 60. To calculate the wear of lower roller 60 the diameter of the lower roller 60 must be measured. To measure the diameter of lower roller 60 with lower roller guard 64 installed, the heavy equipment is lilted, causing the undercarriage 70 to sag allowing access to the lower roller 60. Measuring the lower roller 60 with rock guard 64 installed without lifting the heavy equipment can be accomplished using the undercarriage wear measurement tool 10.

As illustrated in FIG. 5, sleeve 22 of undercarriage wear measurement tool 10 is positioned over a lower roller bolt 52. The undercarriage wear measurement tool 10 fastener magnet 24 securely attaches the undercarriage wear measurement tool 10 to the lower roller bolt 52. The measurement pin 26 is now aligned with the center of the lower roller bolt 52 creating a centered reference point of the lower relief 60 extending beyond the lower roller guard 64. The distance between the center point of the measurement pin 26 and the lower track shoe 66 is measured, illustrated by Measurement B. The track link 68 is measured to determine the track link 68 height, illustrated by Measurement C. The lower roller 60 diameter can now be determined by subtracting Measurement C from Measurement B and multiplying by a factor of 2.

It is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

The foregoing description relates to what is presently considered to be the most practical embodiment. It is to be understood, however, that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

I claim:

1. A undercarriage wear measurement tool, comprising:

a. a housing;

b. a sleeve attached to the housing that centers the undercarriage wear measurement tool over a component;

c. an elongated passage wherein the elongated passage extends from the center of the sleeve through the housing d. a first fastener magnet with respect to the sleeve that attaches the sleeve and housing assembly to the component; and e. an elongated measurement pin comprising:

i. a first end configured to contact the component; and ii. a second end slidably disposed through the elongated passage that provides a diameter measurement reference point, wherein the elongated passage is an aperture through the sleeve and housing assembly, and wherein the elongated measurement pin is configured to penetrate through the length of the elongated passage.

2. The undercarriage wear measurement tool of claim 1 further comprising a flat surface with respect to the housing, wherein the flat surface is configured to attach to the component, wherein the component does not have a bolt head.

* * * * *